US008022055B2

(12) United States Patent
Mukherjee et al.

(10) Patent No.: US 8,022,055 B2
(45) Date of Patent: Sep. 20, 2011

(54) BETULINIC ACID DERIVATIVES

(75) Inventors: Rama Mukherjee, Uttar Pradesh (IN); Sanjay Kumar Srivastava, Uttar Pradesh (IN); Mohammad Jamshed Ahmed Siddiqui, Uttar Pradesh (IN); Manu Jaggi, Uttar Pradesh (IN); Anu T. Singh, Uttar Pradesh (IN); Anand Vardhan, Uttar Pradesh (IN); Manoj Kumar Singh, Uttar Pradesh (IN); Praveen Rajendran, Uttar Pradesh (IN); Hemant Kumar Jajoo, Uttar Pradesh (IN); Anand C. Burman, Uttar Pradesh (IN); Vivek Kumar, Uttar Pradesh (IN); Nidhi Rani, Uttar Pradesh (IN); Shiv Kumar Agarwal, Uttar Pradesh (IN)

(73) Assignee: Dabur Pharma Limited, New Delhi (IN)

( * ) Notice: Subject to any disclaimer, the term of this patent is extended or adjusted under 35 U.S.C. 154(b) by 775 days.

(21) Appl. No.: 11/883,753

(22) PCT Filed: Dec. 29, 2005

(86) PCT No.: PCT/IN2005/000445

§ 371 (c)(1), (2), (4) Date: May 7, 2008

(87) PCT Pub. No.: WO2006/085334

PCT Pub. Date: Aug. 17, 2006

(65) Prior Publication Data

US 2008/0293682 A1 Nov. 27, 2008

(30) Foreign Application Priority Data

Feb. 9, 2005 (IN) ............................ 265/DEL/2005

(51) Int. Cl.
*A61K 31/33* (2006.01)
*A61K 31/40* (2006.01)
*A61K 31/34* (2006.01)

(52) U.S. Cl. ......... 514/183; 514/410; 514/468; 552/510

(58) Field of Classification Search .................. 552/510; 514/183, 410, 468
See application file for complete search history.

(56) References Cited

OTHER PUBLICATIONS

Vippagunta et al. (Advanced Drug Delivery Reviews, 48 (2001), pp. 3-26.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

* cited by examiner

*Primary Examiner* — Barbara P Badio
(74) *Attorney, Agent, or Firm* — Ladas & Parry LLP

(57) ABSTRACT

The invention relates to novel betulinic acid derivatives of formula (I), wherein R is $C(=CH_2)CH_3$ or $CH(CH_3)_2$; $R_2$ together with the adjacent carbonyl group forms a carboxylic acid, carboxylic acid ester or amide or substituted amide; $R_3$ or $R_4$ are hydrogen or aryl with the proviso that both are not independently hydrogen or alkyl or $R_3$ and $R_4$ are combined together to form an aryl ring optionally substituted with a group X, wherein X is selected from halogen, alkyl, cyano, nitro, alkoxy, amino or substituted amine; Y is N or O; and $R_1$ is zero when Y is O, and $R_1$ is hydrogen, alkyl or aryl alkyl when Y is N, useful for inhibition of tumor cancer cells.

(I)

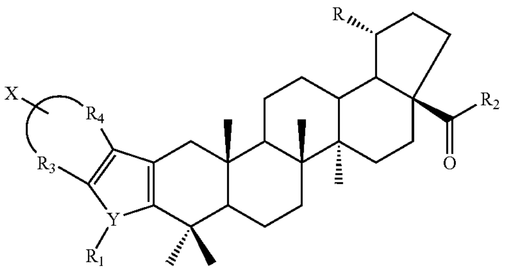

23 Claims, No Drawings

BETULINIC ACID DERIVATIVES

This application is a 371 of PCT/IN2005/000445 filed Dec. 29, 2005.

FIELD OF THE INVENTION

The present invention relates to novel betulinic acid derivatives of formula (I), exhibiting useful activity in the inhibition of tumor cancer cells and in particular possessing improved pharmacokinetics over betulinic acid.

The present invention also relates to a process for preparation of the novel betulinic acid derivatives of formula (I).

The present invention further relates to pharmaceutical compositions comprising the novel betulinic acid derivatives of formula (I) for treatment of cancer.

BACKGROUND OF THE INVENTION

The chemical entity, 33-hydroxy-lup-20(29)-en-28-oic acid, generically known as betulinic acid and represented by the chemical formula (II), (II)

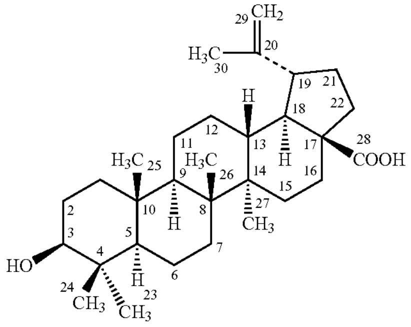

is a naturally occurring pentacyclic triterpenoid (*Journal of Applied Biomedicine,* 2003, 1, 7-12) possessing useful biological properties such as anticancer, anti-inflammatory, antiviral, antiseptic, antimalarial, spermicidal, antimicrobial, antileshmanial, antihelmentic and antifeedent activities. However, amongst all the aforementioned activities, betulinic acid has been found particularly to exhibit anticancer and anti HIV activities (*Journal of Medicinal and Aromatic Plant Sciences,* 2002, 24, 1031-1037).

Earlier, betulinic acid was considered as a melanoma-specific cytotoxic agent, however, recent evidences indicate that it has a broad spectrum of activity against other types of cancer cells (*IDrugs,* 2004, 7(4), 359-373).

Betulinic acid has been selected by NCI, USA for Rapid Access to Intervention Development (RAID) programme. Betulinic acid has been shown to act through the induction of apoptosis irrespective of the cells p-53 and CD-95 status. Some experimental reports indicate that betulinic acid functions through the mitochondrial pathway. The pharmacokinetics and tissue distribution of betulinic acid has also been studied in CD-1 mice but a detailed investigation is required to find out its kinetic behavior (*Biopharm. Drug Dispos.,* 1999, 20, 379-383). A recent study indicates that though betulinic acid has lower potency as compared to doxorubicin, but the former seems to be selective for tumor cells, since minimal toxicity against normal cells was observed (*Cancer Letters,* 2002, 175, 17-25). These findings and favorable therapeutic index, even at dose up to 500 mg/Kg body weight, have made betulinic acid a very promising candidate for the clinical treatment of various forms of cancer (*Medicinal Research Reviews,* 2004, 24(1), 90-114).

As a consequence of the promise betulinic acid holds for treatment of various types of cancer, research in the recent past has been directed towards synthesis and screening of new derivatives of the acid with a view of finding more potent compounds. A summary of the recent advances is given herein below:

At the outset, it might be mentioned that variations of substituents at positions 2, 3, 20 and 28 of betulinic acid molecule of formula (II), has been the subject matter of all research efforts to obtain potent lead compounds, viz, U.S. Pat. No. 6,018,847; U.S. Pat. No. 6,225,353; U.S. Pat. No. 6,369,109;U.S. Pat. No. 6,670,345; WO 98/51293; WO 98/51294; WO 02/16395; WO 02/091858; US 03/0181429; US03/0186945;U.S. Pat. No. 6,403,816.

Recently, isoxazole derivatives of betulinic acid have been reported as cytotoxic agents (*Bioorganic Medicinal Chemistry Letters,* 2003, 13, 3137-3140).

Even though, all the above mentioned reports collectively disclose a large number of betulinic acid derivatives, with a vast majority of them found to possess antitumor activity, however, due to various reasons they are not particularly good candidates, clinically as well as do not have the best of pharmacokinetic properties.

Of all the derivatives of betulinic acid discussed hereinbefore, findings from our laboratory show that one of the molecules disclosed in U.S. Pat. No. 6,403,816 and designated as MJ1098-RS of formula (III) exhibits good in vitro cytotoxicity in various cancer cell lines. U.S. Pat. No. 6,670,345 further discloses that compound of formula (III) also shows tumor reduction in murine xenograft models.

(III)

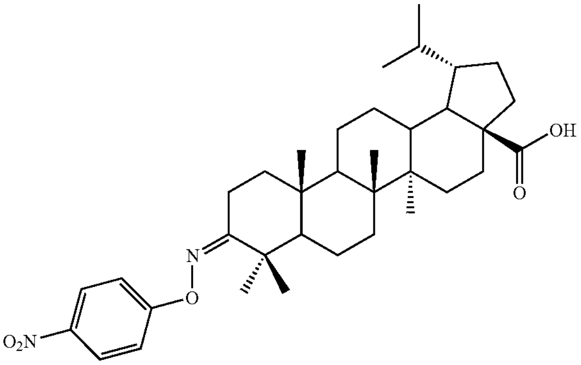

A need therefore, exists for new betulinic acid derivatives, which are not only potent, but also clinically safe and moreover, have better pharmacokinetic properties.

In our efforts to find molecules which are not only potent therapeutically but also acceptable clinically, we have found that substitutions at C-2 and C-3 positions of the betulinic acid of formula (II) with a heterocycle fused to the said positions, imparts the desired characteristics which forms the basis of the present invention.

OBJECTS OF THE PRESENT INVENTION

An object of the present invention is to provide novel betulinic acid derivatives exhibiting antitumor activity.

Another object of the present invention is to provide novel betulinic acid derivatives, which are not only potent therapeutically but also possess improved pharmacokinetics.

Yet another object of the present invention is to provide processes for preparation of novel betulinic acid derivatives.

A further object of the present invention is to provide a pharmaceutical composition of novel betulinic acid derivatives for treatment of cancer.

SUMMARY OF THE INVENTION

In their endeavor to meet the objectives, the present inventors have found that a new class of betulinic acid derivatives could be obtained by substitution of the C-2 and C-3 positions of betulinic acid of formula (II), with a heterocycle fused to the said positions.

In particular, it was found that C-2 and C-3 positions of the betulinic acid of formula (II) substituted through ring fusion at the said C-2 and C-3 positions with a five membered heterocycle afford novel compounds represented by formula (I), which exhibit useful anticancer activity. These derivatives are novel and hitherto not reported.

Amongst a large number of such compounds of formula (I), its pharmaceutically acceptable salts, solvates, their isomers, polymorphs, N-oxide or metabolites, wherein (I)

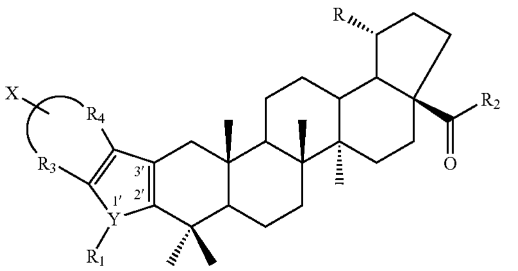

R is $C(=CH_2)CH_3$ or $CH(CH_3)_2$; $R_2$ together with the adjacent carbonyl group forms a carboxylic acid, carboxylic acid ester or amide or substituted amide; $R_3$ or $R_4$ are hydrogen or aryl with the proviso that both are not independently hydrogen or alkyl or $R_3$ and $R_4$ are combined together to form an aryl ring optionally substituted with a group X, wherein X is selected from halogen, alkyl, cyano, nitro, alkoxy, amino or substituted amine; Y is N or O; and $R_1$ is zero when Y is O, and $R_1$ is hydrogen, alkyl or aryl alkyl when Y is N and screened, in particular one of the compound designated as Compound 5, throughout the specification was found to exhibit significant efficacy, i.e., significantly improved anticancer activity over betulinic acid of formula (II) and is comparable to MJ-1098-RS of formula (III). A comparison of the anticancer activity of compound 5 with that of betulinic acid (II) and MJ-1098-RS (III) is given in Table-1.

TABLE 1

Table 1: A comparison of $IC_{50}$ values of in vitro cytotoxicity of betulinic acid derivative (Compound 5) with Betulinic acid (II) and MJ-1098-RS (III)

| Compound | IC50(μg/ml) for cell lines | | | | | | | |
|---|---|---|---|---|---|---|---|---|
| No. | NIH3T3 | PA1 | DU145 | SW620 | HBL100 | Miapaca | A549 | K562 |
| Betulinic Acid (II) | — | 11.53 | >20 | 13.26 | 5.02 | >20 | 3.008 | — |
| MJ1098-RS (III) | — | 3.63 | 0.82 | 3.40 | 2.82 | 3.17 | 1.175 | — |
| Compound 5 | 4.6 ± 0.14 | 2.5 | 4.9 | 2.7 | 11.75 ± 1.65 | 2.44 ± 0.26 | 7.14 ± 0.5 | 9.61 ± 0.78 |

In addition Compound 5 was found to exhibit, significantly superior pharmacokinetic properties over betulinic acid (II) and comparable to that of MJ 1098-RS (III), which would be evident from the comparison in Table-2

TABLE 2

Table 2: Comparision of Pharmacokinetic Properties of Compound 5 with that betulinic acid (II), and MJ-1098-RS (III)

| Parameters | Units | Betulinic acid (II) | MJ-1098-RS (III) | Compound 5 |
|---|---|---|---|---|
| $C_0$ | μg/ml | 36.02 | 100.9 | 132.2 |
| $AUC_{(0-t)}$ | μg * h/ml | 10.63 | | |
| $AUC_{(0-e)}$ | μg * h/ml | 13.94 | 43.6 | 78.4 |
| $K_{el}$ | $h^{-1}$ | 2.60 | | |
| $T_{1/2}$ | h | 0.265 | 9.9 | 6.7 |
| $V_d$ | ml | 41.6 | 0.6 | 0.23 |

The pharmacokinetic parameters indicate that betulinic acid analogue MJ-1098 (III) and Compound 5 provide better systemic exposure ($AUC_{0-\infty}$) and slower elimination ($K_{el}$) as compared to betulinic acid. This should result in a significantly better therapeutic response as compared to betulinic acid.

Representative salts of the compounds of formula (I) include but are not limited to the following: acetate, ascorbate, benzoate, citrate, oxalate, stearate, trifluoroacetate, succinate, tartarate, lactate, fumarate, gluconate, glutamate, phosphate/diphosphate, and valerate. Other salts include Ca, Li, Mg, Na, and K salts, halides, salts of amino acids such as lysine or arginine; guanidine, ammonium, substituted ammonium salts or aluminium salts.

Pharmaceutical compositions comprising the compounds of formula (I), its salts etc. was found to be useful for inhibiting the multiplication of cancer cells in humans. In particular, the pharmaceutical compositions are found to be useful in treatment of humans, mammals or others suffering from cancer or other tumors.

The representative compounds that are encompassed under formula (I) are summarized in Table-3.

TABLE 3

Table-3: The representative compounds encompassed under formula (I)

| Compound No. | X | Y | R | $R_1$ | $R_2$ | $R_3$ | $R_4$ |
|---|---|---|---|---|---|---|---|
| 1 | H | N | $C(=CH_2)CH_3$ | H | OH | Ph | |
| 2 | H | N | $CH(CH_3)_2$ | H | OH | Ph | |
| 3 | H | N | $C(=CH_2)CH_3$ | $CH_3$ | OH | Ph | |
| 4 | H | N | $CH(CH_3)_2$ | $CH_3$ | OH | Ph | |
| 5 | 5'-Cl | N | $C(=CH_2)CH_3$ | H | OH | Ph | |
| 6 | 5'-Cl | N | $CH(CH_3)_2$ | H | OH | Ph | |
| 7 | 5'-F | N | $C(=CH_2)CH_3$ | H | OH | Ph | |
| 8 | 5'-F | N | $CH(CH_3)_2$ | H | OH | Ph | |
| 9 | 7'-Cl | N | $C(=CH_2)CH_3$ | H | OH | Ph | |
| 10 | 5'-$OCH_3$ | N | $C(=CH_2)CH_3$ | H | OH | Ph | |
| 11 | H | O | $C(=CH_2)CH_3$ | — | OH | Ph | |
| 12 | H | O | $CH(CH_3)_2$ | — | OH | Ph | |
| 13 | — | N | $CH(CH_3)_2$ | $C_6H_5CH_2$ | OH | H | Ph |
| 15 | H | N | $C(=CH_2)CH_3$ | H | $—OCH_2Ph$ | Ph | |
| 16 | H | N | $CH(CH_3)_2$ | H | $—OCH_2Ph$ | Ph | |
| 17 | H | N | $C(=CH_2)CH_3$ | H | $OCH_2C(O)OC(CH_3)_3$ | Ph | |
| 18 | H | N | $C(=CH_2)CH_3$ | H | $OCH_2CH=CH_2$ | Ph | |
| 19 | 5'-Cl | N | $C(=CH_2)CH_3$ | H | $—OCH_2Ph$ | Ph | |
| 21 | H | N | $C(=CH_2)CH_3$ | H | $—NHCH_2CO_2CH_3$ | Ph | |
| 22 | H | N | $C(=CH_2)CH_3$ | H | $—NHCH_2CO_2H$ | Ph | |
| 23 | 5'-Cl | N | $C(=CH_2)CH_3$ | H | $—NHCH_2CO_2CH_3$ | Ph | |
| 24 | 5'-Cl | N | $C(=CH_2)CH_3$ | H | $—NHCH_2CO_2H$ | Ph | |
| 25 | 5'-Cl | N | $C(=CH_2)CH_3$ | H | 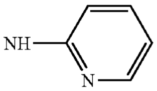 | Ph | |
| 26 | 5'-Cl | N | $C(=CH_2)CH_3$ | H | 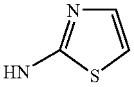 | Ph | |
| 27 | 5'-Cl | N | $C(=CH_2)CH_3$ | H | $—NHCH_2C\equiv CH$ | Ph | |
| 28 | 5'-Cl | N | $C(=CH_2)CH_3$ | $C_6H_5CH_2$ | $—NHCH_2CO_2H$ | Ph | |
| 29 | H | N | $C(=CH_2)CH_3$ | $C_6H_5CH_2$ | $—NHCH_2CO_2H$ | Ph | |
| 30 | 5'-Cl, 7'-Cl | N | $C(=CH_2)CH_3$ | H | OH | Ph | |
| 31 | 4'-Cl, 6'-Cl | N | $C(=CH_2)CH_3$ | H | OH | Ph | |
| 32 | 5'-Cl | N | $C(=CH_2)CH_3$ | H | $—NHC_6H_4CF_3$ (4") | Ph | |
| 33 | 5'-Cl | N | $C(=CH_2)CH_3$ | H | $—NHC_6H_4OCF_3$ (4") | Ph | |
| 34 | 5'-Cl | N | $C(=CH_2)CH_3$ | H | 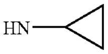 | Ph | |
| 35 | 5'-Cl | N | $C(=CH_2)CH_3$ | H | 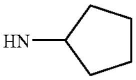 | Ph | |

These improved cytotoxicity profile and pharmacokinetics properties render the novel betulinic acid derivatives of formula (I) of this invention as vastly superior candidates for treatment of dancer.

In another aspect, the present invention provides novel betulinic acid derivatives of formula (I) exhibiting useful activity in inhibition of tumor cancer cells.

In yet another aspect, the present invention provides a compound of formula (I), which shows improved pharmacokinetics over betulinic acid of formula (II) and comparable to that of MJ-1098-RS of formula (III).

In a further aspect, present invention provides a process of preparation of novel betulinic acid derivatives of formula (I).

In yet further aspect, the present invention provides a pharmaceutical composition comprising compounds of formula (I) for treatment of cancer.

DETAILED DESCRIPTION OF THE INVENTION

The compounds of formula (I), can be prepared from betulonic acid of formula (IV) or 20,29-dihydrobetulonic acid of formula (V)

(IV)

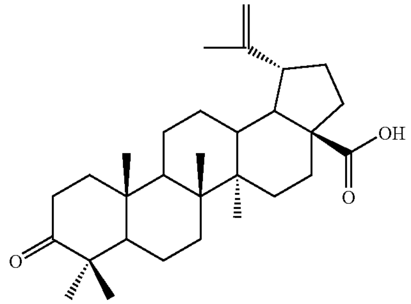

(V)

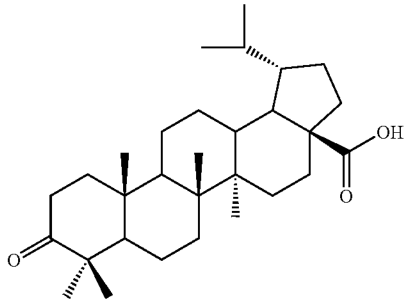

The starting compounds of formula (IV) and (V) can be prepared as per the method described in U.S. Pat. No. 6,670,345.

Compound No. 1 to 10, 30 and 31 of Table-3 can be prepared by reaction of betulonic acid of formula (IV) or 20,29-dihydrobetulonic acid of formula (V) with appropriate hydrazines or its hydrochloride salt. The reaction can be carried out in the presence or absence of hydrochloric acid and in presence of suitable solvents for example, ethanol, methanol and isopropanol at a temperature ranging from 0 to 100° C.

Compound No. 11 to 12 of Table-3 can be prepared by reaction of betulonic acid of formula (IV) or 20,29-dihydrobetulonic acid of formula (V) with appropriate O-phenylhydroxylamine or its hydrochloride salt. The reaction can be carried out in the presence or absence of hydrochloric acid and in presence of suitable solvents, for example, ethanol, methanol and isopropanol at a temperature ranging from 0 to 100° C.

Compound No. 13 of Table-3 can be prepared by reaction of betulonic acid of formula (IV) with appropriate amines and appropriate β-nitrostyrenes. The reaction can be carried out in the presence or absence of para-toluenesulfonic acid and in the absence or presence molecular sieves and in presence of suitable solvent, for example, ethanol, methanol and isopropanol at a temperature ranging from 0 to 100° C.

Compound No. 15 to 19 of Table-3 can be prepared by reaction of Compound No. 14 with suitable halides. The reaction can be carried out in the presence of suitable base, for example, potassium carbonate or triethylamine and in presence of suitable solvent, for example, acetone and ether at a temperature ranging from 0 to 100° C.

Compound No. 20 can be prepared by reaction of Compound No. 14 with oxalyl chloride. The reaction can be carried in the presence or absence of a solvent at a temperature ranging from 0° C. to room temperature.

Compound No. 21, 23, 25 to 27 and 32 to 35 of Table-3 can be prepared by reaction of Compound No. 20 with suitable amines. The reaction can be carried out in the presence of suitable solvents, for example, methylene chloride, chloroform, carbon tetrachloride, acetone and ether at a temperature ranging from 0 to 100° C.

Compound No. 22 and 24 can be prepared by reaction of Compound No. 21 and 23 with aqueous sodium hydroxide solution, respectively. The reaction can be carried out in the presence of suitable solvents, for example, tetrahydrofuran, ethanol and methanol at a temperature ranging from 0 to 100° C.

Compound No. 28 and 29 Table-3 can be prepared by reaction of Compound No. 23 and 21 with benzyl bromide and sodium hydrazide, respectively. The reaction can be carried out in the presence of suitable solvents, for example, hexamethyl phosphoramide at a temperature ranging from 0° C. to room temperature.

The methods of preparation of compounds 1 to 35 of Table-3 are summarized in Schemes 1, 2 and 3.

Scheme 1

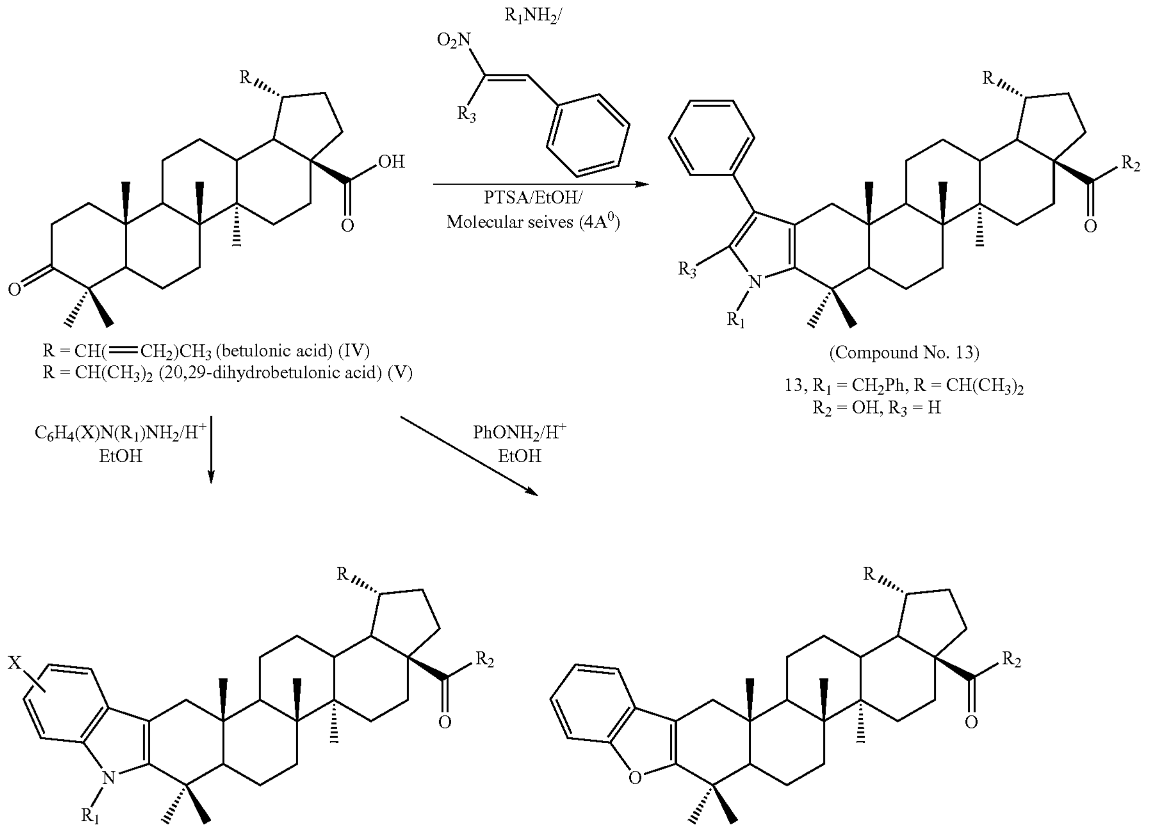

R = CH(=CH₂)CH₃ (betulonic acid) (IV)

R = $CH(CH_3)_2$ (20,29-dihydrobetulonic acid) (V)

(Compound No. 13)

13, $R_1 = CH_2Ph$, R = $CH(CH_3)_2$ $R_2$ = OH, $R_3$ = H (Compound No. 1 to 10)

$R_2$ = OH

1, X = H, $R_1$ = H, R = $C(=CH_2)CH_3$

2, X = H, $R_1$ = H, R = $CH(CH_3)_2$

3, X = H, $R_1 = CH_3$, R = $C(=CH_2)CH_3$

4, X = H, $R_1 = CH_3$, R = $CH(CH_3)_2$

5, X = 5'-Cl, $R_1$ = H, R = $C(=CH_2)CH_3$

6, X= 5'-Cl, $R_1$ = H, R = $CH(CH_3)_2$

7, X = 5'-F, $R_1$ = H, R = $C(=CH_2)CH_3$

8, X = 5'-F, $R_1$ = H, R = $CH(CH_3)_2$

9, X = 7'-Cl, $R_1$ = H, R = $C(=CH_2)CH_3$

10, X = 5'-$OCH_3$, $R_1$ = H, R = $C(=CH_2)CH_3$

30, X = 5'-Cl, 7'-Cl, $R_1$ = H, R = $C(=CH_2)CH_3$

31, X = 4'-Cl, 6'-Cl, $R_1$ = H, R = $C(=CH_2)CH_3$ (Compound No. 11 and 12)

$R_2$ = OH

11, R = $C(=CH_2)CH_3$

12, R = $CH(CH_3)_2$

Scheme 2:

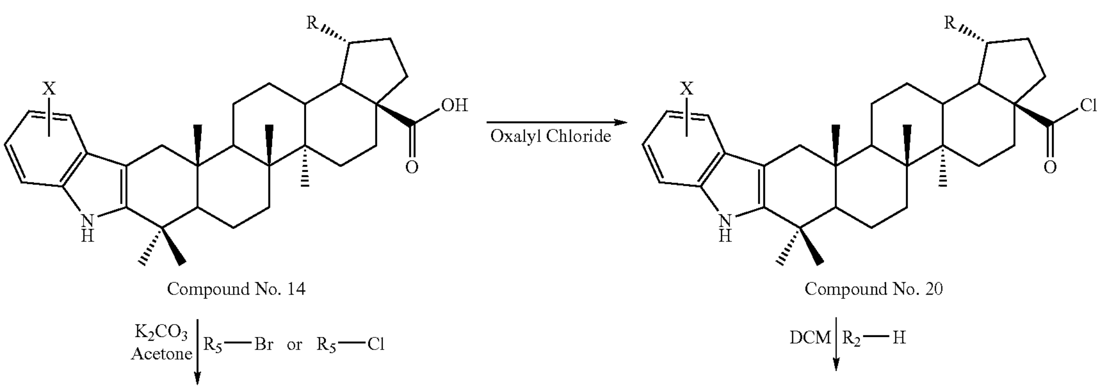

Compound No. 14

Compound No. 20

-continued

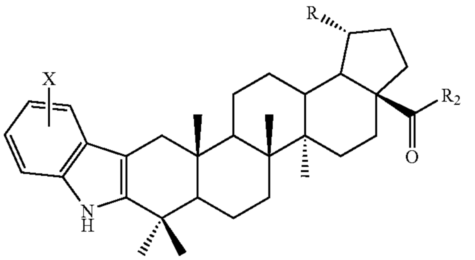

Compound No. 15 to 19

$R_2$ ═ $OR_5$

15, X = H, $R_5$ = $CH_2P$
R = $C(═CH_2)CH_3$
16, X = H, $R_5$ = $CH_2Ph$, R = $CH(CH_3)_2$
17, X = H, $R_5$ = $CH_2C(O)OC(CH_3)_3$,
R = $C(═CH_2)CH_3$
18, X = H, $R_5$ = $CH_2CH═CH_2$,
R = $C(═CH_2)CH_3$
19, X = 5'-Cl, $R_5$ = $CH_2Ph$,
R = $C(═CH_2)CH_3$
21, X = H, $R_2$ = $NHCH_2CO_2CH_3$
R = $C(═CH_2)CH_3$
22, X = H, $R_2$ = $NHCH_2CO_2H$
R = $C(═CH_2)CH_3$
23, X = 5'-Cl, $R_2$ = $NHCH_2CO_2CH_3$
R = $C(═CH_2)CH_3$
24, X= 5'-Cl, $R_2$ = $NHCH_2CO_2H$
R = $C(═CH_2)CH_3$
25, X = 5'-Cl, $R_2$ = HN 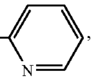,
R = $C(═CH_2)CH_3$
26, X = 5'-Cl, $R_2$ = HN 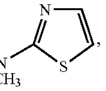,
R = $C(═CH_2)CH_3$
27, X = 5'-Cl, $R_2$ = NHC≡CCH,
R = $C(═CH_2)CH_3$
32, X = 5'-Cl, $R_2$ = —$NHC_6H_4CF_3(4''$-)
R = $C(═CH_2)CH_3$
33, X = 5'-Cl, $R_2$ = —$NHC_6H_4OCF_3(4''$-)
R = $C(═CH_2)CH_3$
34, X = 5'-Cl, $R_2$ = HN 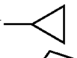
R = $C(═CH_2)CH_3$
35, X = 5'-Cl, $R_2$ = HN 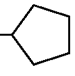
R = $C(═CH_2)CH_3$

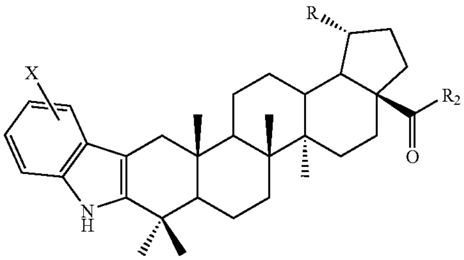

Compound No. 21, 23, 25 to 27 and 32 to 35

Compound No. 22
4 N aq. NaOH
THF/MeOH (1:1)

4 N aq. NaOH
THF/MeOH (1:1)
Compound No. 24

Scheme 3:

21 or 23
$C_6H_5CH_2Br$
NaH/HMPA

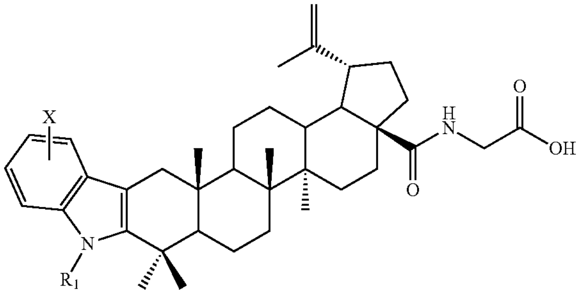

28, X = 5'-Cl, $R_1$ = $CH_2C_6H_5$
29, X = H, $R_1$ = $CH_2C_6H_5$,

As would be evident, the betulinic acid derivatives of formula (I) (Compound 1-13, 30 and 31) of the present invention may be synthesized by the reaction sequence as shown in scheme 1 while few betulinic acid derivatives of formula (I) (Compound 15-29 and 32-35) of the present invention may be synthesized by the reaction sequence as shown in scheme 2 and 3.

The pharmaceutically acceptable salts, pharmaceutically acceptable solvates, their isomers, polymorphs, N-oxides and metabolites of these derivatives can be prepared by methods known in the art.

The synthesis of compounds of formula (I) is further described in the following examples, which however should not be construed as limiting scope of the invention.

Betulinic acid (II) was purchased from Dabur Pharma Ltd. Kalyani, W B, India. Solvents and reagents were purchased from different companies such as Aldrich, Lancaster, Acros, Rankem, Qualigens Fine Chemicals, Spectrochem, SD Fine Chem, and Merck and used as supplied. All the betulinic acid derivatives were purified on column chromatography using silica gel (100-200 mesh) as adsorbent and dichloromethane/methanol or hexane/ethyl acetate combinations as eluent. All TLC data ($R_f$-values) were determined with aluminum sheets coated with silica gel 60 $F_{254}$ (Merck). Nuclear Magnetic Resonance (NMR) spectra were recorded on a Bruker 300 MHz instrument using tetramethylsilane (TMS) as an internal standard. Mass spectra were recorded on a Micromass Quattro Micro™ instrument. The purity of betulinic acid derivatives was determined on Shimadzu HPLC LC-2010 C HT instrument using gradient system. Melting points were obtained in a capillary tubes with a thermal scientific melting point apparatus MP-1 and are uncorrected.

The following abbreviation are used in the present invention: pTSA (para toluenesulfonic acid), DCM (dichloromethane or methylene chloride), $CHCl_3$ (chloroform), EtOAc (ethyl acetate), MeOH (methanol), EtOH (ethanol), THF (tetrahydrofuran), NaOH (sodium hydroxide), $Na_2CO_3$ (sodium carbonate), $K_2CO_3$ (potassium carbonate) and $Na_2SO_4$ (sodium sulphate).

The starting material betulonic acid (IV) and 20,29-dihydrobetulonic acid (V) were synthesized from betulinic acid and 20,29-dihydrobetulinic acid respectively as disclosed in U.S. Pat. No. 6,670,345.

Example-1

General Procedure for the Synthesis of Compounds as Described Under Formula I (Compound No. 1-12, 30 and 31)

Betulonic acid (IV) or 20,29-dihydrobetulonic acid (V) (1 eq) and appropriate hydrazine or its hydrochloride (1.1 eq) are dissolved in solvent ethanol. To the solution, 2-3 drops of 3N HCl was added and allowed to reflux for 6-9 hours. Solvent was then removed in vacuuo and residue was extracted with water and EtOAc or DCM. The organic layer was separated, dried over $Na_2SO_4$ and then evaporated to afford the crude product. The product was purified by column using DCM or DCM/MeOH or EtOAc/Hexane as eluent.

Example-2

General Procedure for the Synthesis of Compounds as Described Under Formula I (Compound No. 13)

To the solution of betulonic acid (IV) or 20,29-dihydrobetulonic acid (V) (1 eq) in solvent ethanol, amine (1.1 eq), para-toluenesulfonic acid monohydrate (catalytic amount) and molecular sieves (4A°) were added. The reaction mixture was allowed to reflux for 2 hours. It was cooled and appropriate β-nitrostyrene (1 eq) was then added. It was allowed to reflux for additional 7 hours. It was then cooled and filtered. The solvent was evaporated in vacuuo and the residue, thus obtained, was washed with hexane. The product was purified by column using DCM or DCM/MeOH or EtOAc/Hexane as eluent.

Example-3

General Procedure for the Synthesis of Compounds as Described Under Formula I (Compound No. 15-19)

A mixture of compound 14 (1 eq) and $K_2CO_3$ (1.5 eq) in solvent acetone was stirred for 30 minutes. Appropriate bromide or chloride (2.5 eq) was added, and the mixture was stirred overnight. The bromide or chloride (1.5 eq) was again added and stirred for 24 hours at room temperature. The solvent was evaporated in vacuuo and the residue, thus obtained, was washed with water and hexane. It was then extracted with DCM. The organic layer was combined, dried over $Na_2SO_4$ and then evaporated to furnish a crude product. The product was purified by column using DCM or DCM/MeOH or EtOAc/Hexane as eluent.

Example-4

General Procedure for the Synthesis of Betulonoyl Chloride Derivatives (Compound No. 20)

Compound 14 (1 eq) was dissolved in DCM and oxalyl chloride (1.5 eq) was added and stirred for 6 hours at room temperature. It was then evaporated; washed with water, treated with aqueous $Na_2CO_3$ solution and extracted with DCM. The combined organic layer was dried over $Na_2SO_4$ and then evaporated in vacuuo to afford the betulonoyl chloride derivative 20, which was used for next step without purification.

Example-5

General Procedure for the Synthesis of Compounds as Described Under Formula I (Compound No. 21-27 and 32 to 35)

Amine (2 eq) was added to the solution of appropriate betulonoyl chloride derivative 20 (1 eq) in DCM and stirred over night at room temperature. The solvent was then evaporated in vacuuo and the residue, thus obtained, was washed with water and hexane. It was then extracted with DCM. The organic layer was combined, dried over $Na_2SO_4$ and then evaporated to furnish a crude product. The product was purified by column using DCM or DCM/MeOH or EtOAc/Hexane as eluent.

Hydrolysis of Compounds No. 21 and 23 was carried out using 4N aqueous NaOH solution in solvent THF/MeOH (1:1) to provide Compounds No. 22 and 24, respectively.

Example-6

General Procedure for the Synthesis of Compounds as Described Under Formula I (Compound No. 28-29)

Sodium hydride (NaH) (1.1 eq) was added to the solution of compounds no. 23 or 21 in hexamethylphosphoramide (HMPA) at 0° C. under nitrogen atmosphere and stirred for 10 minutes. It was further stirred for 5 hours at room temperature. Benzyl bromide (1 eq.) was added at 0° C. and stirred for overnight at ambient temperature. It was then diluted with water and extracted with EtOAc. The organic layer was combined, dried over $Na_2SO_4$ and then evaporated to furnish a crude product. The obtained product was purified by column using DCM as eluent.

The spectral characteristics of the different compounds of formula (I) as represented in Table-3 are given below:

2,3-Didehydroindolo[2',':2,3]betulinic acid (1)

$R_f$ 0.72 (2% MeOH/DCM); $^1$HNMR ($CDCl_3$) δ values 7.69 (bs, 1H), 7.39-7.25 (m, 2H), 7.12-7.02 (m, 2H), 4.7 (bs, 1H), 4.64 (bs, 1H), 3.1-2.9 (m, 1H), 2.83 (d, 1H, J=14.9 Hz), 2.28-1.98 (m, 4H), 1.82-1.38 (m, 20H), 1.27 (s, 3H), 1.16 (s, 3H), 1.03 (s, 6H), 0.86 (s, 3H); MS m/z (% relative intensity) 528 (100); HPLC purity 97.48%.

2,3-Didehydro-20,29-dihydroindolo[2',3':2,3]betulinic acid (2)

$R_f$ 0.59 (2% MeOH/$CHCl_3$); $^1$HNMR ($CDCl_3$) δ values 7.68 (bs, 1H), 7.42-7.40 (m, 1H), 7.29-7.24 (m, 1H), 7.13-

7.03 (m, 2H), 2.84 (d, 1H, J=14.9 Hz), 2.3-1.98 (m, 3H), 1.9-1.24 (m, 23H), 1.15 (s, 3H), 1.02-0.85 (m, 12H), 0.78 (d, 31-1, J=6.7 Hz); MS m/z (% relative intensity) 529 (100); HPLC purity 96.87%.

2,3-Didehydro-1'-methylindolo[2',':2,3]betulinic acid (3)

$R_f$ 0.88 (2% MeOH/DCM); $^1$HNMR ($CDCl_3$) δ values 7.45-7.42 (m, 1H), 7.29-7.17 (m, 2H), 7.12-7.07 (m, 1H), 4.83 (bs, 1H), 4.69 (bs, 1H), 3.86 (s, 3H), 3.2-3.05 (m, 1H), 2.92 (d, 1H, J=14.9 Hz), 2.45-2.0 (m, 4H), 1.98-1.44 (m, 23H), 1.31 (s, 3H), 1.08 (s, 6H), 0.91 (s, 3H). MS m/z (% relative intensity) 540 (100); HPLC purity 94.94%.

2,3-Didehydro-20,29-dihydro-1'-methylindolo[2',3', 2,3]betulinic acid (4)

$R_f$ 0.83 (2% MeOH/DCM); $^1$HNMR ($CDCl_3$) δ values 7.45-7.43 (m, 1H), 7.28-7.16 (m, 2H), 7.11-7.06 (m, 1-H), 3.85 (s, 3H), 2.9 (d, 1H, J=14.9 Hz), 2.45-2.15 (m, 3H), 2.14-1.20 (m, 26H), 1.08-0.83 (m, 12H), 0.80 (d, 3H, 0.1=6.6 Hz); MS m/z (% relative intensity) 542 (100); HPLC purity 89.29%.

5'-Chloro-2,3-didehydroindolo[2',':2,3]betulinic acid (5)

$R_f$0.62 (2% MeOH/DCM); $^1$HNMR ($CDCl_3$) δ values 7.73 (bs, 1H), 7.36 (s, 1H), 7.07-7.06 (m, 1H), 7.04-7.03 (m, 1H), 4.78 (bs, 1H), 4.65 (bs, 1H), 3.14-3.0 (m, 1H), 2.80 (d, 1H, J=15.0 Hz), 2.32-2.27 (m, 2H), 2.2-1.99 (m, 3H), 1.77-1.26 (m, 22H), 1.18 (s, 31-1), 1.03 (s, 6H), 0.85 (s, 3H); MS m/z (% relative intensity) 560 (100); HPLC purity 99.09%.

5'-Chloro-2,3-didehydro-20,29-dihydroindolo[2',':2, 3]betulinic acid (6)

$R_f$0.9 (2% MeOH/DCM); $^1$HNMR ($CDCl_3$) δ values 7.66 (bs, 1H), 7.29 (d, 1H, J=1.9 Hz), 7.13-7.10 (m, 1H), 6.99-6.96 (m, 1H), 2.70 (d, 1H, J=15.1 Hz), 2.32-2.19 (m, 3H), 2.10-1.96 (m, 1H), 1.85-1.68 (m, 2H), 1.64-1.18 (m, 20H), 1.09 (s, 3H), 0.94 (s, 6H), 0.83-0.78 (m, 6H), 0.71 (d, 3H, J=6.6 Hz); MS m/z (% relative intensity) 562 (100); HPLC purity 98.38%.

2,3-Didehydro-5'-fluoroindolo[2',':2,3]betulinic acid (7)

$R_f$0.63 (2% MeOH/DCM); $^1$HNMR ($CDCl_3$) δ values 7.68 (bs, 1H), 7.20-7.15 (m, 1H), 7.03-6.89 (m, 1H), 6.87-6.80 (m, 1H), 4.78 (bs, 1H), 4.64 (bs, 1H), 3.20-3.06 (m, 1H), 2.74 (d, 1H, J=14.9 Hz), 2.36-2.19 (m, 2H), 2.15-1.98 (m, 3H), 1.80-1.26 (m, 22H), 1.17 (s, 3H), 1.03 (s, 6H), 0.86 (s, 3H); MS m/z (% relative intensity) 544 (100); HPLC purity 93.36%.

2,3-Didehydro-5'-fluoro-20,29-dihydroindolo[2',':2, 3]betulinic acid (8)

$R_f$0.82 (2% MeOH/DCM); $^1$HNMR ($CDCl_3$) δ values 7.68 (bs, 1H), 7.20-7.16 (m, 1H), 7.06-7.02 (m, 1H), 6.87-6.80 (m, 1H), 2.76 (d, 1H, J=14.9 Hz), 2.30-2.10 (m, 4H), 1.95-1.85 (m, 2H), 1.80-1.25 (m, 20H), 1.17 (s, 3H), 1.01 (s, 6H), 0.90-0.87 (m, 6H), 0.78 (d, 3H, J=6.6 Hz); MS m/z (% relative intensity) 546 (100); HPLC purity 99.14%.

7'-Chloro-2,3-didehydroindolo[2',':2,3]betulinic acid (9)

$R_f$0.76 (2% MeOH/DCM); $^1$HNMR ($CDCl_3$) δ values 7.85 (bs, 1H), 7.28-7.26 (m, 1H), 7.09 (d, 1H, J=7.3 Hz), 7.0-6.95 (m, 1H), 4.77 (bs, 1H), 4.64 (bs, 1H), 3.05-2.95 (m, 1H), 2.79 (d, 1H, J=15.1 Hz), 2.32-2.2 (m, 2H), 2.18-1.98 (m, 3H), 1.90-1.33 (m, 13H), 1.31-1.21 (m, 12H), 1.03 (s, 6H), 0.86 (s, 3H); MS m/z (% relative intensity) 560 (100); HPLC purity 91.16%.

2,3-Didehydro-5'-methoxyindolo[2',':2,3]betulinic acid (10)

$R_f$0.3 (DCM); $^1$HNMR ($CDCl_3$) δ values 7.50 (bs, 1H), 7.09 (d, 1H, J=8.6 Hz), 6.78 (d, 1H, J=2.3 Hz), 6.70-6.66 (m, 1H), 4.70 (bs, 1H), 4.56 (bs, 1H), 3.76 (s, 3H), 3.1-2.9 (m, 1H), 2.72 (d, 1H, J=14.9 Hz), 2.30-2.15 (m, 2H), 2.09-1.85 (m, 3H), 1.80-1.25 (m, 13H), 1.21-1.18 (m, 9H), 1.09 (s, 3H), 0.96 (s, 6H), 0.80 (s, 3H); MS m/z (% relative intensity) 556 (100); HPLC purity 99.45%.

2,3-Didehydrobenzfurano[2',3':2,3]betulinic acid (11)

$R_f$0.38 (DCM); $^1$HNMR ($CDCl_3$) δ values 7.41-7.31 (m, 2H), 7.19-7.15 (m, 2H), 4.78 (bs, 1H), 4.64 (bs, 1H), 3.12-2.90 (m, 1H), 2.70 (d, 1H), 2.4-2.2 (m, 2H), 2.19-1.98 (m, 3H), 1.90-1.25 (m, 22H), 1.2 (s, 3H), 1.03 (s, 6H), 0.89 (s, 3H); MS m/z (% relative intensity) 527 (100); HPLC purity 93.83%.

2,3-Didehydro-20,29-dihydrobenzfurano[2',3':2,3] betulinic acid (12)

$R_f$ 0.87 (2% MeOH/DCM); ($CDCl_3$) δ values 7.42-7.34 (m, 2H), 7.20-7.16 (m, 2H), 2.71 (d, 1H, J=15.2 Hz), 2.35-2.10 (m, 3H), 2.0-1.2 (m, 26H), 1.02-0.87 (m, 12H), 0.78 (d, 3H, J=6.7 Hz); MS m/z (% relative intensity) 529 (100); HPLC purity 90.89%.

1'-Benzyl-2,3-didehydro-20,29-dihydro-4'-phenylpyrrolo[2',':2,3]betulinic acid (13)

$R_f$ 0.75 (2% MeOH/DCM); $^1$HNMR ($CDCl_3$) δ values 7.37-7.28 (m, 8H), 7.19-6.99 (m, 2H), 6.63 (s, 1H), 5.29 (bs, 2H), 2.79 (d, 1H, J=14.6 Hz), 2.37-2.12 (m, 3H), 1.99-1.80 (m, 2H), 1.78-0.79 (m, 39H); MS m/z (% relative intensity) 646 (100); HPLC purity 83.86%.

28-O-Benzyl-2,3-didehydro[2',3':2,3]indolobetulinate (15)

$R_f$0.9 (2% MeOH/DCM); $^1$HNMR ($CDCl_3$) δ values 7.73 (bs, 1H), 7.40-7.28 (m, 6H), 7.14-7.06 (m, 3H), 5.15 (dd, 2H, J=12.3, 20.4 Hz), 4.78 (bs, 1H), 4.64 (bs, 1H), 3.10-3.07 (m, 1H), 2.84 (d, 1H, J=14.8 Hz), 2.4-2.0 (m, 3H), 1.98-1.29 (m, 24H), 1.20 (s, 3H), 1.02 (s, 6H), 0.87 (s, 3H); MS m/z (% relative intensity) 618 (100); HPLC purity 94.56%.

28-O-Benzyl-2,3-didehydro-20,29-dihydro[2',3':2,3] indolobetulinate (16)

$R_f$ 0.8 (DCM); $^1$HNMR ($CDCl_3$) δ values 7.68 (bs, 1H), 7.34-7.19 (m, 6H), 7.05-6.97 (m, 3H), 5.04 (dd, 2H, J=12.3, 17.4 Hz), 2.85 (d, 1H, J=14.9 Hz), 2.48-2.30 (m, 3H), 2.02-

1.20 (m, 23H), 1.0 (s, 3H), 0.91-0.85 (m, 12H), 0.79 (d, 3H, J=6.7 Hz); MS m/z (% relative intensity) 620 (100); HPLC purity 97.8%.

28-O-Pivaloyoxymethyl-2,3-didehydroindolo[2',3':2,3]betulinate (17)

$R_f$ 0.87 (2% MeOH/DCM); $^1$HNMR ($CDCl_3$) δ values 7.90 (bs, 1H), 7.42 (d, 1H, J=7.0 Hz), 7.30 (d, 1H, J=7.3 Hz), 7.16-7.06 (m, 2H), 5.83 (dd, 2H, J=5.4, 11.0 Hz), 4.81 (bs, 1H), 4.68 (bs, 1H), 3.08-3.05 (m, 1H), 2.86 (d, 1H, J=14.9 Hz), 2.4-2.1 (m, 3H), 2.0-1.8 (m, 2H), 1.75-1.22 (m, 3H), 1.06 (s, 6H), 0.90 (s, 3H); MS m/z (% relative intensity) 664 (100), 642 (37); HPLC purity 92.19%.

28-O-Allyl-2,3-didehydroindolo[2',3':2,3]betulinate (18)

$R_f$ 0.4 (20% EtOAc/Hexane); $^1$HNMR ($CDCl_3$) δ values 7.71 (bs, 1H), 7.38-7.37 (m, 1H), 7.3-7.28 (m, 1H), 7.10-7.04 (m, 2H), 6.0-5.9 (m, 1H), 5.37-5.25 (m, 2H), 4.77 (bs, 1H), 4.63-4.58 (m, 3H), 3.15-3.05 (m, 1H), 2.83 (d, 1H, J=14.9 Hz), 2.45-2.05 (m, 3H), 2.0-1.8 (m, 2H), 1.75-1.01 (m, 31H), 0.86 (s, 3H); MS m/z (% relative intensity) 566 (95), 113 (100); HPLC purity 100%.

28-O-Benzyl-5'-chloro-2,3-didehydroindolo[2',':2,3]betulinate (19)

$R_f$ 0.5 (20% EtOAc/Hexane); $^1$HNMR ($CDCl_3$) δ values 7.67 (bs, 1H), 7.30-7.25 (m, 6H), 7.11-7.08 (m, 1H), 6.98-6.94 (m, 1H), 5.06 (dd, 2H, J=12.3, 20.9 Hz), 4.68 (bs, 1H), 4.55 (bs, 1H), 3.10-2.90 (m, 1H), 2.68 (d, 1H, J=15.0 Hz), 2.30-1.95 (m, 3H), 1.9-1.85 (m, 2H), 1.75-1.0 (m, 25H), 0.92 (s, 3H), 0.76-0.75 (m, 6H); MS m/z (% relative intensity) 650 (100); HPLC purity 100%.

28-N-Methylglycinate-2,3-didehydroindolo[2',3':2,3]betulinamide (21)

$R_f$ 0.53 (2% MeOH/DCM); $^1$HNMR ($CDCl_3$) δ values 7.69 (bs, 1H), 7.31 (d, 1H, J=7.2 Hz), 7.21 (d, 1H, J=7.7 Hz), 7.05-6.97 (m, 2H), 6.01 (bs, 1H), 4.70 (bs, 1H), 4.55 (bs, 1H), 3.97-3.94 (m, 2H), 3.69 (s, 3H), 3.2-3.0 (m, 1H), 2.74 (d, 1H, J=14.9 Hz), 2.6-2.3 (m, 1H), 2.2-1.8 (m, 3H), 1.78-1.70 (m, 2H), 1.68-0.95 (m, 30H), 0.78 (s, 3H); MS m/z (% relative intensity) 621 (100), 599 (60); HPLC purity 93.43%.

28-N-Glycine-2,3-didehydroindolo[2',3':2,3]betulinamide (22)

$R_f$ 0.43 (7% MeOH/DCM); $^1$HNMR ($CDCl_3$) δ values 7.70 (bs, 1H), 7.37 (d, 1H, J=7.4 Hz), 7.30-7.27 (m, 1H), 7.12-7.04 (m, 2H), 6.13 (bs, 1H), 4.77 (bs, 1H), 4.62 (bs, 1H), 4.09-4.06 (m, 2H), 3.15-3.12 (m, 1H), 2.83 (d, 1H, J=14.9 Hz), 2.6-2.45 (m, 1H), 2.2-1.88 (m, 3H), 1.85-1.70 (m, 2H), 1.68-1.01 (m, 30H), 0.86 (s, 3H); MS m/z (% relative intensity) 583 (100); HPLC purity 97.59%.

28-N-Methylglycinate-5'-chloro-2,3-didehydroindolo[2',3':2,3]betulinamide (23)

$R_f$ 0.5 (2% MeOH/DCM); $^1$HNMR ($CDCl_3$) δ values 7.73 (bs, 1H), 7.32 (d, 1H, J=1.7 Hz), 7.18 (d, 1H, J=8.4 Hz), 7.05-7.02 (m, 1H), 6.06 (t, 1H, J=5.0 Hz), 4.77 (bs, 1H), 4.63 (bs, 1H), 4.04-4.02 (m, 2H), 3.76 (s, 3H), 3.25-3.1 (m, 1H), 2.76 (d, 1H, J=15.0 Hz), 2.6-2.4 (m, 1H), 2.15-1.95 (m, 3H), 1.9-1.75 (m, 2H), 1.70-1.01 (m, 30H), 0.84 (s, 3H); MS m/z (% relative intensity) 633 (100); HPLC purity 100%.

28-N-Glycine-5'-chloro-2,3-didehydroindolo[2',3':2,3]betulinamide (24)

$R_f$ 0.31 (7% MeOH/DCM); $^1$HNMR ($CDCl_3$) δ values 7.67 (bs, 1H), 7.25 (s, 1H), 7.11 (d, 1H, J=8.4 Hz), 6.97-6.95 (m, 1H), 6.2 (bs, 1H), 4.69 (bs, 1H), 4.55 (bs, 1H), 3.93 (bs, 2H), 3.2-2.95 (m, 1H), 2.68 (d, 1H, J=15.0 Hz), 2.5-2.3 (m, 1H), 2.25-1.85 (m, 5H), 1.8-0.75 (m, 33H); MS m/z (% relative intensity) 617 (100); HPLC purity 100%.

28-N-(2"-pyridine)-5'-chloro-2,3-didehydroindolo[2',': 2,3]betulinamide (25)

$R_f$ 0.7 (2% MeOH/DCM); $^1$HNMR ($CDCl_3$) δ values 8.18-8.15 (m, 2H), 8.08 (bs, 1H), 7.76 (bs, 1H), 7.62 (t, 1H, J=7.6 Hz), 7.26 (s, 1H), 7.08 (d, 1H, J=8.4 Hz), 6.97-6.94 (m, 2H), 4.72 (bs, 1H), 4.58 (bs, 1H), 3.2-3.05 (m, 1H), 2.69 (d, 1H, J=15.0 Hz), 2.65-2.55 (m, 1H), 2.04-1.9 (m, 5H), 1.87-1.09 (m, 25H), 1.03 (s, 3H), 0.96-0.93 (m, 2H), 0.76 (s, 3H); MS m/z (% relative intensity) 638 (100); HPLC purity 95.81%.

28-N-(2"-thiazole)-5'-chloro-2,3-didehydroindolo[2',': 2,3]betulinamide (26)

$R_f$ 0.59 (2% MeOH/DCM); $^1$HNMR ($CDCl_3$) δ values 9.9 (bs, 1H), 7.72 (bs, 1H), 7.45 (d, 1H, J=3.4 Hz), 7.33 (s, 1H), 7.17 (d, 1H, J=8.4 Hz), 7.05-6.97 (m, 2H), 4.81 (bs, 1H), 4.66 (bs, 1H), 3.25-3.1 (m, 1H), 2.76 (d, 1H, J=14.8 Hz), 2.65-2.55 (m, 1H), 2.25-1.8 (m, 5H), 1.75-1.26 (m, 21H), 1.17 (s, 3H), 1.04-0.97 (m, 6H), 0.83 (s, 3H); MS m/z (% relative intensity) 644 (100); HPLC purity 91.43%.

28-N-Propargyl-5'-chloro-2,3-didehydroindolo[2',':2,3]betulinamide (27)

$R_f$ 0.68 (DCM); $^1$HNMR ($CDCl_3$) δ values 7.71 (bs, 1H), 7.33 (d, 1H, J=1.5 Hz), 7.17 (d, 1H, J=8.5 Hz), 7.05-7.02 (m, 1H), 5.71 (bs, 1H), 4.77 (bs, 1H), 4.63 (bs, 1H), 4.08-4.0 (m, 2H), 3.25-3.1 (m, 1H), 2.76 (d, 1H, J=15.0 Hz), 2.6-2.45 (m, 1H), 2.2-1.95 (m, 3H), 1.9-1.25 (m, 2H), 1.18 (s, 3H), 1.02 (s, 6H), 0.84 (s, 3H); MS m/z (% relative intensity) 599 (100); HPLC purity 98.01%.

28-N-Glycine benzyl-5'-chloro-2,3-didehydroindolo[2',':2,3]betulinamide (28)

$R_f$ 0.5 (DCM); $^1$HNMR ($CDCl_3$) δ values 7.73 (s, 1H), 7.36-7.33 (m, 5H), 7.18 (d, 1H, J=8.4 Hz), 7.05-7.02 (m, 1H), 6.06 (t, 1H), 5.23-5.14 (m, 2H), 4.77 (bs, 1H), 4.62 (bs, 1H), 4.08-4.06 (m, 2H), 3.15-3.09 (m, 1H), 2.76 (d, 1H, J=14.9 Hz), 2.56-2.49 (m, 1H), 2.11-1.8 (m, 5H), 1.64-0.99 (m, 31H), 0.83 (s, 3H); MS m/z (% relative intensity) 709 (20), 731 (100); HPLC purity 96.6%.

28-N-Glycine benzyl-2,3-didehydroindolo[2',3':2,3]betulinamide (29)

$R_f$ 0.6 (DCM); $^1$HNMR ($CDCl_3$) δ values 7.71 (s, 1H), 7.37-7.26 (m, 6H), 7.12-7.02 (m, 2H), 6.07 (bs, 1H), 5.19 (s, 2H), 4.77 (bs, 1H), 4.62 (bs, 1H), 4.07 (d, 2H, J=4.5 Hz), 3.15-3.1 (m, 1H), 2.81 (d, 1H, J=15.0 Hz), 2.56-2.48 (m, 1H), 2.13 (d, 1H, J=15.0 Hz), 2.0-1.79 (m, 4H), 1.64-1.0 (m, 31H), 0.85 (s, 3H); MS m/z (% relative intensity) 675 (10), 697 (100); HPLC purity 98.6%.

2,3-Didehydro-5',7'-dichloroindolo[2',3':2,3]betulinic acid (30)

$R_f$ 0.7 (DCM); $^1$HNMR ($CDCl_3$) δ values 7.85 (bs, 1H), 7.25 (d, 2H, J=3.0 Hz), 4.78 (bs, 1H), 4.65 (bs, 1H), 3.1-3.0 (m, 1H), 2.74 (d, 1H, J=15.0 Hz), 2.32-2.23 (m, 2H), 2.09 (d, 1H, J=15.0 Hz), 2.04-1.97 (m, 2H), 1.81 (d, 1H, J=12.0 Hz), 1.64-1.25 (m, 22H), 1.19 (s, 3H), 1.02 (s, 6H), 0.84 (s, 3H); MS m/z (% relative intensity) 594 (100); HPLC purity 91.6%.

2,3-Didehydro-4',6'-dichloroindolo[2',3':2,3]betulinic acid (31)

$R_f$ 0.4 (20% EtOAc/Hexane); $^1$HNMR ($CDCl_3$) δ values 7.79 (bs, 1H), 7.14 (s, 1H), 6.98 (s, 1H), 4.78 (bs, 1H), 4.64 (bs, 1H), 3.3 (d, 1H, J=15.6 Hz), 3.1-3.0 (m, 1H), 2.32-2.22 (m, 3H), 2.05-1.98 (m, 2H), 1.79 (d, 1H, J=12.6 Hz), 1.64-1.25 (m, 22H), 1.17 (s, 3H), 1.02 (s, 6H), 0.87 (s, 3H); MS m/z (% relative intensity) 594 (100); HPLC purity 98.6%.

28-N-(4"-Trifluoromethyl)phenyl-5'-chloro-2,3-didehydroindolo[2',3':2,3]betulinamide (32)

$R_f$ 0.3 (20% EtOAc/Hexane); $^1$HNMR ($CDCl_3$) δ values 7.72 (bs, 1H), 7.65-7.56 (m, 3H), 7.38 (s, 1H), 7.33 (d, 1H, J=1.8 Hz), 7.18 (d, 1H, J=8.5 Hz), 7.06-7.02 (m, 1H), 4.78 (bs, 1H), 4.66 (bs, 1H), 3.22-3.19 (m, 1H), 2.79-2.66 (m, 2H), 2.4-2.2 (m, 1H), 2.2-1.8 (m, 5H), 1.56-1.01 (m, 30H), 0.84 (s, 3H); MS m/z (% relative intensity) 703 (100); HPLC purity 90%.

28-N-(4"-Trifluoromethoxy)benzyl-5'-chloro-2,3-didehydroindolo[2',':2,3]betulinamide (33)

$R_f$ 0.8 (DCM); $^1$HNMR ($CDCl_3$) δ values 7.68 (bs, 1H), 7.27-7.24 (m, 3H), 7.12-7.09 (m, 3H), 6.98-6.95 (m, 1H), 5.89 (t, 1H), 4.7 (bs, 1H), 4.56 (bs, 1H), 4.44-4.42 (m, 1H), 4.3-4.28 (m, 1H), 3.13-3.11 (m, 1H), 2.69 (d, 1H, J=14.9 Hz), 2.5-2.3 (m, 1H), 2.1-1.74 (m, 5H), 1.57-1.1 (m, 2H), 0.94 (s, 3H), 0.86 (s, 3H), 0.77 (s, 3H); MS m/z (% relative intensity) 735 (55), 757 (100); HPLC purity 97.3%.

28-N-Cyclopropyl-5'-chloro-2,3-didehydroindolo[2',':2,3]betulinamide (34)

$R_f$ 0.3 (DCM); $^1$HNMR ($CDCl_3$) δ values 7.71 (bs, 1H), 7.33 (s, 1H), 7.18 (d, 1H, J=8.4 Hz), 7.05-7.02 (m, 1H), 5.67 (bs, 1H), 4.76 (bs, 1H), 4.62 (bs, 1H), 3.21-3.18 (m, 1H), 2.76 (d, 1H, J=14.9 Hz), 2.67-2.65 (m, 1H), 2.53-2.51 (m, 1H), 2.1-1.7 (m, 5H), 1.55-1.01 (m, 30H), 1.0-0.8 (m, 6H), 0.45-0.44 (m, 1H); MS m/z (% relative intensity) 601 (100); HPLC purity 98.1%.

28-N-Cyclopentyl-5'-chloro-2,3-didehydroindolo[2',3':2,3]betulinamide (35)

$R_f$ 0.5 (DCM); $^1$HNMR ($CDCl_3$) δ values 7.66 (bs, 1H), 7.25 (d, 1H, J=1.7 Hi), 7.11 (d, 1H, J=8.4 Hz), 6.98-6.95 (m, 1H), 5.4 (d, 1H, J=6.9 Hz), 4.7 (bs, 1H), 4.55 (bs, 1H), 4.15-4.09 (m, 1H), 3.12-3.09 (m, 1H), 2.68 (d, 1H, J=14.9 Hz), 2.47-2.45 (m, 1H), 2.05-1.7 (m, 5H), 1.56-0.95 (m, 38H), 0.77 (s, 3H); MS m/z (% relative intensity) 629 (85), 651 (100); HPLC purity 97.5%.

A PubMed search of the National Library of Medicine was carried out to determine the relevance of cell lines used by us for determining the anticancer activity of the peptides. While DU145 (human prostate) showed 829 "hits" when searched with reference to cancer, other human cancer cell lines used by us also showed large number of hits (3047 for A549, 349 for PA-1 and 134 for Miapaca.2). This clearly shows the extensive use of these cell lines in cancer research. Further, it is a common and standard practice and norm for testing molecules for anticancer activity in vitro on human tumor cell lines. (*Br J. Cancer.* 2001 May 18; 84(10):1289-90 (Flasks, Fibres and Flanks—Preclinical tumor models for predicting clinical antitumor activity). The authors report that in vitro activity against 6 or more lung or breast cancer cell lines does predict xenograft activity against these tumor types. In articles "Semin Oncol 1992 December; 19(6):622-38 (*The National Cancer Institute: cancer drug discovery and development program*) and "*Jpn J. Antibiot.,* 1977 December; 30 Suppl: 35-40 (Antitumor screening procedures of the National Cancer Institute)" extensive use of human tumor cell lines for identification of potential cytotoxic drugs is described."

In Vitro Cytotoxicity of Compounds of Formula (I)

A number of compounds listed in Table-3 were tested for cytotoxicity against prostate, lung, laryngeal, pancreas, breast, colon and ovarian cancer, leukemia and lymphoma, human tumor cell lines. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophotometrically. MIT was dissolved in phosphate buffered saline with a pH of 7.4 to obtain an MIT concentration of 5 mg/ml; the resulting mixture was filtered through a 0.22-micron filter to sterilize and remove a small amount of insoluble residue. For each type of tumor cell, 10,000 to 15,000 cells were seeded in a 96-well culture plate and incubated with the individual betulinic acid derivatives in a $CO_2$ incubator for a total of 72 hours. Control cells not treated with the betulinic acid derivatives were similarly incubated. The assay was terminated by adding 100 μg (20 μl) of MIT to each well then incubating for additional one hour, and finally adding 50 μl of 10% SDS-0.01N HCl to each well to lyse the cells and dissolve formazan. After incubating for one hour, the plate was read spectrophotometrically at 540 nm and the percentage of cytotoxicity calculated using the following formula:

$$\text{Cytotoxicity percentage}=100\times[1-(X/R_1)],$$

where X=(absorbance of treated sample at 540 nm)−(absorbance of blank at 540 nm) $R_1$=absorbance of control sample at 540 nm.

The $IC_{50}$ Values of the cytotoxicity defined as the concentration at which 50% of the cells are killed in vitro was calculated for each cell line treated with each of the betulinic acid derivatives.

The $IC_{50}$ values of in vitro cytotoxicity of betulinic acid derivatives of formula (I) are shown in the Table 4.

NIH3T3 Cytotoxicity Test

The cytotoxic effect of chemicals upon NIH 3T3 cells in culture is measured by cell metabolism determination using the previously described MIT assay. Healthy NIH 3T3 cells (an established cell-line), when maintained in culture continuously divide and multiply over time. The basis of this test is that a cytotoxic chemical (regardless of site or mechanism of action) will interfere with this process and, thus, result in a reduction of the growth rate as reflected by cell number. The degree of inhibition of growth, related to the concentration of the test compound, provides an indication of toxicity.

The NIH 3T3 cells are maintained in culture and exposed to test compounds over a range of concentrations and the number of viable cells determined after 72 hours exposure by MIT assay. The number of cells in the presence of test chemicals are compared to that observed in control cultures and the percent inhibition of growth calculated. The $IC_{50}$ concentration (i.e. the concentration producing 50% inhibition of growth) is determined and expressed as μg/ml. A ratio of $IC_{50}$ of NIH 3T3 cells to tumor cells is an indicator of predicted toxicity of the molecule and is represented as “Safety Index”. The higher the value, the better is the predicted safety of the molecule. Table 5 shows the $IC_{50}$ values on NIH 3T3 cells and the safety index of the molecules in various cell lines.

TABLE 4

$IC_{50}$ values of in vitro cytotoxicity of betulinic acid derivatives

| Compound | IC50 (μg/ml) for cell lines | | | | | | | |
|---|---|---|---|---|---|---|---|---|
| No. | NIH3T3 | PA1 | DU145 | SW620 | HBL100 | Miapaca | A549 | K562 |
| 1 | 6.9 ± 0.76 | 6.01 | 8.86 | 5.151 | 10.3 ± 0.9 | 6.7 ± 0.59 | 7.6 ± 0.57 | 10.05 ± 0.61 |
| 2 | >20 | >20 | >20 | >20 | >20 | >20 | >20 | 15.07 ± 2.15 |
| 3 | 15.12 ± 3.04 | ND | 20 | ND | 19.5 ± 2.1 | 5.34 ± 0.96 | 6.9 ± 0.21 | 7.73 ± 0.17 |
| 4 | >20 | >20 | >20 | ND | 14.14 ± 0.8 | 5.4 ± 0.43 | 6.5 ± 3.4 | 10.85 ± 1.5 |
| 5 | 4.6 ± 0.14 | 2.5 | 4.9 | 2.7 | 11.75 ± 1.65 | 2.44 ± 0.26 | 7.14 ± 0.5 | 9.61 ± 0.78 |
| 6 | 19.03 ± 0.21 | 6.6 | 6.5 | 5.9 | >20 | 15.19 ± 1.06 | 8.8 ± 0.74 | >20 |
| 7 | >20 | ND | ND | 9.16 | >20 | 17.4 ± 2.6 | 17.8 ± 1.79 | 10.95 ± 0.93 |
| 8 | 14.59 ± 0.33 | ND | ND | 7.28 | >20 | 8.4 ± 0.76 | 8.89 ± 0.84 | 14.01 ± 0.75 |
| 9 | 11.8 ± 0.19 | 6.39 | 11.66 | 2.008 | 11.8 ± 0.35 | 11.6 ± 0.49 | 8.7 ± 0.19 | 9.26 ± 1.6 |
| 10 | 7.5 ± 0.48 | 5.8 | 5.75 | 8.4 | 12.8 ± 0.39 | 6.4 ± 0.44 | 8.2 ± 0.14 | >20 |
| 11 | 19.03 ± 0.79 | >20 | >20 | >20 | >20 | >20 | >20 | >20 |
| 12 | 20 ± 5.6 | >20 | >20 | ND | >20 | 8.8 ± 0.36 | 7.1 ± 1.6 | 15.28 ± 0.18 |
| 13 | >20 | >20 | >20 | >20 | >20 | >20 | ND | ND |
| 15 | >20 | >20 | >20 | >20 | >20 | >20 | >20 | >20 |
| 16 | >20 | >20 | >20 | >20 | >20 | >20 | >20 | >20 |
| 17 | >20 | >20 | >20 | >20 | >20 | >20 | >20 | >20 |
| 18 | >20 | >20 | >20 | >20 | >20 | >20 | >20 | >20 |
| 19 | >20 | >20 | >20 | >20 | >20 | >20 | >20 | >20 |
| 21 | >20 | >20 | >20 | >20 | >20 | >20 | >20 | >20 |
| 22 | 0.68 ± 0.003 | 3.0 | 7.0 | 8.7 | >20 | 0.67 ± 0.03 | 3.53 ± 0.82 | 11.92 ± 1.37 |
| 23 | >20 | >20 | >20 | >20 | >20 | >20 | >20 | >20 |
| 24 | 11.2 ± 0.63 | 6.66 | 10.32 | 10.42 | 16.5 ± 0.6 | 10.7 ± 0.63 | 12.4 ± 1.78 | >20 |
| 25 | >20 | >20 | >20 | >20 | >20 | >20 | >20 | >20 |
| 26 | >20 | >20 | >20 | >20 | >20 | >20 | >20 | >20 |
| 27 | >20 | >20 | >20 | >20 | >20 | >20 | >20 | >20 |
| 31 | 4.10 | >20 | >20 | >20 | >20 | >20 | 5.5 | >20 |
| 34 | 1.82 | >20 | >20 | >20 | >20 | >20 | >20 | >20 |

TABLE 5

$IC_{50}$ values on NIH 3T3 cells and the safety index of the molecules in various cell lines.

| Compound | Specific Index (SI) for cell lines | | | |
|---|---|---|---|---|
| No. | HBL100 | Miapaca | A549 | K562 |
| 1 | 0.669 | 1.029 | 0.907 | 0.68 |
| 3 | 0.775 | 2.831 | 2.191 | 1.956 |
| 4 | >1.414 | >3.703 | >3.076 | >1.843 |
| 5 | 0.391 | 1.885 | 0.644 | 0.478 |
| 6 | <0.951 | 1.252 | 2.163 | <0.952 |
| 7 | Can not be determined | >1.149 | >1.123 | >1.826 |
| 8 | <0.730 | 1.737 | 1.641 | 1.041 |
| 9 | 1 | 1.017 | 1.356 | 1.274 |
| 10 | 0.586 | 1.172 | 0.915 | <0.38 |
| 11 | <0.952 | <0.952 | <0.952 | <0.952 |
| 12 | <1 | 2.273 | 2.817 | 1.309 |
| 22 | <0.034 | 1.015 | 0.913 | 0.057 |
| 24 | 0.679 | 1.047 | 0.903 | <0.56 |

Pharmacokinetic Studies

The pharmacokinetic behavior of the betulinic acid (II), MJ-1098-RS (III) and Compound 5 according to the invention was studied in three Male Wistar rats (150-180 g) after administration at a dose of 10 mg/kg by intravenous injection. Blood samples were taken at various times after administration and plasma was prepared and frozen at −20° C. until analysis. The plasma sample were analyzed by a suitable HPLC method using a C-18 column. The pH of water is adjusted to 3.0 with phosphoric acid. Start the gradient with 70% acetonitrile for 5 minutes and increase the concentration up to 100% within 25 minutes followed by hold at 100% for 10 minutes. It is thus possible to construct the curve showing the plasma concentration as a function of time and to determine different pharmacokinetic parameter of compound studied. The WinNonlin software was used to calculate the pharmacokinetic parameters, which are summarized in Table 2.

The results given in the table 2 shows that the plasma concentrations of the MJ-1098-RS and Compound 5 are quite high and long lasting as compared to betulinic acid (II). The compounds according to invention therefore have very advantageous pharmacokinetic parameters that would make it possible substantially to reduce the amount of active principal used and number of daily administration that are necessary for a given therapeutic effect. Further studies are in progress to evaluate these compounds for preclinical development. In vivo efficacy studies in murine xenograft model and safety studies are also in progress, which shall be included in the complete application.

As mentioned hereinbefore, pharmaceutical compositions comprising the compounds of formula (I), its salts etc. was found to be useful for inhibiting the multiplication of cancer cells in humans. In particular, the pharmaceutical compositions are found to be useful in treatment of humans, mammals or others suffering from cancer or other tumors.

The pharmaceutical compositions may contain pharmaceutically acceptable additives known in the art such as carriers, diluents etc. Typical carriers that can be employed include a disintegrant and a lubricant. Disintegrants and lubricants are well known in the pharmaceutical sciences. Suitable disintegrants include starch, croscarmellose sodium, crospovidone, sodium starch glycolate, croscarmellose calcium, microcrystalline cellulose and polacralin potassium, and the like. Suitable lubricants include magnesium stearate, sodium stearyl fumarate, hydrogenated vegetable oil, hydrogenated castor oil, hydrogenated cottonseed oil, stearic acid and calcium stearate, colloidal silicon dioxide and the like.

The disintegrant and lubricant are selected such that they provide an effective disintegrating amount of the disintegrant and/or an effective lubricating amount of the lubricant, respectively. For example, a typical formulation can contain from 0% to 30% by weight of a disintegrant and 0% to 10% by weight of a lubricant. In a preferred embodiment the formulation contains from 1% to 10% by weight of a disintegrant and 0.2 to 2% by weight of a lubricant.

In addition, the composition can contain other additives, such as suspending agents, thickening agents, preservatives, pH modifiers, bulking agents and flavouring agents.

Examples of suitable suspending agents include xanthan gum, hydroxypropylmethylcellulose, methylcellulose, carageenan, sodium carboxymethyl cellulose, and sodium carboxymethyl cellulose/microcrystalline cellulose mixes, particularly sodium carboxymethyl cellulose/microcrystalline cellulose mixtures.

Suitable suspending agents are thixotropic suspending agents such as xanthan, carageenan and sodium carboxymethyl cellulose/microcrystalline cellulose mixes and mixtures thereof. More preferred of these are xanthan gum and guar gum.

The thickening agents found suitable in the present formulation include silicon dioxide.

The water soluble preservatives found useful in the present invention include sodium benzoate, sodium citrate and benzalkonium chloride, the preferred one being sodium benzoate.

The sweeteners that can be used include sugars such as fructose, sucrose, glucose, maltose, or lactose as well as non caloric sweetener such as aspartame, which can be used alone or in combination with another non-caloric or low caloric sweetener known to have synergistic sweetening properties with aspartame, e.g. saccharin, acesulfame, thaumatin, chalcone, cyclamate, stevioside and the like. The sweetener compositions are more economical and impart good sweetness without after-taste.

The composition may optionally and preferably contain pharmaceutically acceptable diluents, excipients, solvents, binders, stabilizers, and the like. Such diluents may include: RPMI 1649, buffered saline, isotonic NaCl, Ringer's solution, water, distilled water, polyethylene glycol (neat or in water), 2% Tween in water, dimethylsulfoxide to 50% in water, propylene glycol (neat or in water), phosphate buffered saline, balanced salt solution, glycerol, and other conventional fluids that are suitable for intravenous administration. Pharmaceutical composition which provide from about 0.1 to 10 gram (preferably 0.5 to 5.0 gram) of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration.

The methods of this invention comprise, consist of administering systematically to the mammal a therapeutically effective composition of derivatives of betulinic acid of formula (I). An effective dose of betulinic acid derivatives or pharmaceutically acceptable salts of the betulinic acid derivatives of formula (I) ranges from 1 mg/Kg. body weight to 300 mg/Kg. body weight (preferably 10-100 mg)/Kg. body weight) of the mammal, with the dose dependence on the effects sought, the manner of administration, and the cancer being treated. Systemic administration refers to oral, rectal, nasal, transdermal, and parental (i.e., intramuscular, intravenous and subcutaneous). In accordance with good clinical practice, it is preferred to administer the composition at a dose that will produce anticancer effects without causing undue harmful side effects. The composition may be administered either alone or as a mixture with other therapeutic agents such as 5-fluorouracil, methotrexate, etoposide, paclitaxel, taxotere, doxorubicin, daunarubicin, vincristine, vinblastine and other similarly known and established anticancer drugs.

The compounds of general formula (I) and compositions including the compounds of general formula (I) can be used for the inhibition and/or prevention of cancer of the prostate, lung, laryngeal, pancreas, breast, colon and ovarian cancer, leukemia and lymphoma.

The invention claimed is:

1. A compound of formula (I)

(I)

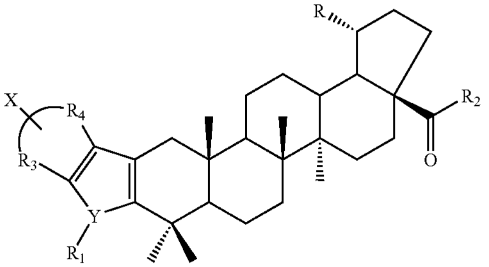

or a pharmaceutically acceptable salt thereof wherein,

R is $C(=CH_2)CH_3$ or $CH(CH_3)_2$;

$R_2$ together with the adjacent carbonyl group forms a carboxylic acid, carboxylic acid ester, amide or substituted amide;

$R_3$ and $R_4$ are combined together to form an aryl ring optionally substituted with a group X, wherein X is selected from the group consisting of hydrogen, halogen, alkyl, and alkoxy;

Y is N or O; and $R_1$ is absent when Y is O; and $R_1$ is hydrogen, alkyl or aryl alkyl when Y is N.

2. The compound as claimed in claim 1, wherein R is $C(=CH_2)CH_3$; Y is N; $R_1$ is hydrogen; $R_2$ together with the adjacent carbonyl group forms a carboxylic acid; $R_3$ and $R_4$ are combined together to form an aryl ring which is substituted with a group X and wherein X is a halogen atom.

3. The compound as claimed in claim 1, wherein R is $C(=CH_2)CH_3$; Y is N; $R_1$ is hydrogen; $R_2$ is $—NHCH_2COOH$; $R_3$ and $R_4$ are combined together to form a aryl ring which is substituted with a group X; wherein X is hydrogen.

4. The compound as claimed in claim 1 wherein said compound of formula is selected from:

| Compound No. | X | Y | R | $R_1$ | $R_2$ | $R_3$ $R_4$ |
|---|---|---|---|---|---|---|
| 1 | H | N | $C(=CH_2)CH_3$ | H | OH | Ph |
| 2 | H | N | $CH(CH_3)_2$ | H | OH | Ph |
| 3 | H | N | $C(=CH_2)CH_3$ | $CH_3$ | OH | Ph |
| 4 | H | N | $CH(CH_3)_2$ | $CH_3$ | OH | Ph |
| 5 | 5'-Cl | N | $C(=CH_2)CH_3$ | H | OH | Ph |
| 6 | 5'-Cl | N | $CH(CH_3)_2$ | H | OH | Ph |
| 7 | 5'-F | N | $C(=CH_2)CH_3$ | H | OH | Ph |
| 8 | 5'-F | N | $CH(CH_3)_2$ | H | OH | Ph |
| 9 | 7'-Cl | N | $C(=CH_2)CH_3$ | H | OH | Ph |
| 10 | 5'-$OCH_3$ | N | $C(=CH_2)CH_3$ | H | OH | Ph |
| 11 | H | O | $C(=CH_2)CH_3$ | — | OH | Ph |
| 12 | H | O | $CH(CH_3)_2$ | — | OH | Ph |
| 15 | H | N | $C(=CH_2)CH_3$ | H | $-OCH_2Ph$ | Ph |
| 16 | H | N | $CH(CH_3)_2$ | H | $-OCH_2Ph$ | Ph |
| 17 | H | N | $C(=CH_2)CH_3$ | H | $OCH_2C(O)OC(CH_3)_3$ | Ph |
| 18 | H | N | $C(=CH_2)CH_3$ | H | $OCH_2CH=CH_2$ | Ph |
| 19 | 5'-Cl | N | $C(=CH_2)CH_3$ | H | $-OCH_2Ph$ | Ph |
| 21 | H | N | $C(=CH_2)CH_3$ | H | $-NHCH_2CO_2CH_3$ | Ph |
| 22 | H | N | $C(=CH_2)CH_3$ | H | $-NHCH_2CO_2H$ | Ph |
| 23 | 5'-Cl | N | $C(=CH_2)CH_3$ | H | $-NHCH_2CO_2CH_3$ | Ph |
| 24 | 5'-Cl | N | $C(=CH_2)CH_3$ | H | $-NHCH_2CO_2H$ | Ph |
| 25 | 5'-Cl | N | $C(=CH_2)CH_3$ | H | 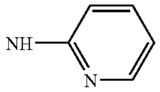 | Ph |
| 26 | 5'-Cl | N | $C(=CH_2)CH_3$ | H | 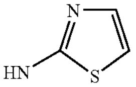 | Ph |
| 27 | 5'-Cl | N | $C(=CH_2)CH_3$ | H | $-NHCH_2C\equiv CH$ | Ph |
| 28 | 5'-Cl | N | $C(=CH_2)CH_3$ | $C_6H_5CH_2$ | $-NHCH_2CO_2H$ | Ph |
| 29 | H | N | $C(=CH_2)CH_3$ | $C_6H_5CH_2$ | $-NHCH_2CO_2H$ | Ph |
| 30 | 5'-Cl, 7'-Cl | N | $C(=CH_2)CH_3$ | H | OH | Ph |
| 31 | 4'-Cl, 6'-Cl | N | $C(=CH_2)CH_3$ | H | OH | Ph |
| 32 | 5'-Cl | N | $C(=CH_2)CH_3$ | H | $-NHC_6H_4CF_3$ (4") | Ph |
| 33 | 5'-Cl | N | $C(=CH_2)CH_3$ | H | $-NHC_6H_4OCF_3$ (4") | Ph |
| 34 | 5'-Cl | N | $C(=CH_2)CH_3$ | H | 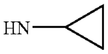 | Ph |
| 35 | 5'-Cl | N | $C(=CH_2)CH_3$ | H | 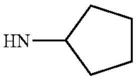 | Ph. |

5. A composition comprising a therapeutically effective amount of a compound of formula (I) according to claim 1 in presence of one or more of a pharmaceutically acceptable carrier, adjuvant or diluent.

6. A composition comprising a therapeutically effective amount of a compound of formula (I) according to claim 2 in presence of one or more of a pharmaceutically acceptable carrier, adjuvant or diluent.

7. A composition comprising a therapeutically effective amount of a compound of formula (I) according to claim 3 in presence of one or more of a pharmaceutically acceptable carrier, adjuvant or diluent.

8. A method of treating a cancer in a mammal in need of such treatment comprising administering to the mammal a therapeutically effective amount of a pharmaceutical composition as defined in claim 5.

9. A method of treating a cancer in a mammal in need of such treatment comprising administering to the mammal a therapeutically effective amount of a pharmaceutical composition as defined in claim 6.

10. A method of treating a cancer in a mammal in need of such treatment comprising administering to the mammal a therapeutically effective amount of a pharmaceutical composition as defined in claim 7.

11. A process for preparing a compound of formula (I)

(I)

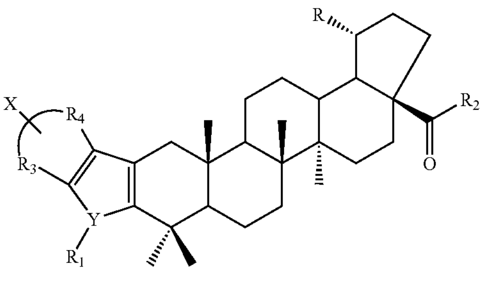

wherein R is $C(=CH_2)CH_3$ or $CH(CH_3)_2$;

$R_2$ together with the adjacent carbonyl group forms a carboxylic acid, carboxylic acid ester or amide or substituted amide;

$R_3$ and $R_4$ are combined together to form an aryl ring optionally substituted with a group X, wherein X is selected from the group consisting of hydrogen, halogen, alkyl, and alkoxy;

Y is N or O; and $R_1$ is hydrogen, alkyl or aryl alkyl reacting wherein the process comprises the steps of:

reacting a Betulonic acid of formula (IV) or 20,29-dihydrobetulonic acid of formula (V)

(IV)

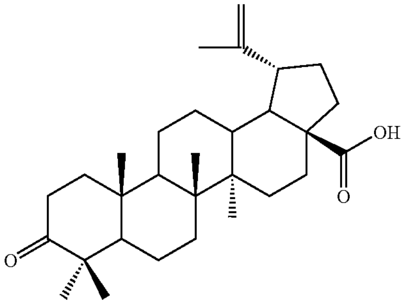

(V)

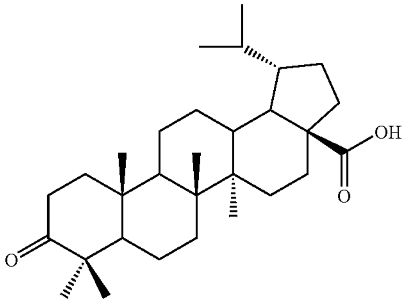

with a hydrazine or its hydrochloride salt and an acid catalytic agent in the presence of a $C_1$ to $C_4$ alcohol as solvent.

12. A process as claimed in claim 11, wherein in formula (I)

(i) X=H, $R_1$=H, R=C(=CH$_2$)CH$_3$;

(ii) X=H, $R_1$=H, R=CH(CH$_3$)$_2$, (iii) X=H, $R_1$=CH$_3$, R=C(=CH$_2$)CH$_3$;

(iv) X=H, $R_1$=CH$_3$, R=CH(CH$_3$)$_2$, (v) X=5'-Cl, $R_1$=H, R=C(=CH$_2$)CH$_3$, (vi) X=5'-Cl, $R_1$=H, R=CH(CH$_3$)$_2$;

(vii) X=5'-F, $R_1$=H, R=C(=CH$_2$)CH$_3$;

(viii) X=5'-F, $R_1$=H, R=CH(CH$_3$)$_2$;

(ix) X=7'-Cl, $R_1$=H, R=C(=CH$_2$)CH$_3$;

(x) X=5'-OCH$_3$, $R_1$=H, R=C(=CH$_2$)CH$_3$;

(xi) X=5'—Cl, 7'-Cl, $R_1$=H, R=C(=CH$_2$)CH$_3$;

(xii) X=4'-Cl, 6'-Cl, $R_1$=H, R=C(=CH$_2$)CH$_3$;

(xiii) R=C(=CH$_2$)CH$_3$; or (xiv) R=CH(CH$_3$)$_2$.

13. A process for preparing a compound of formula (I)

(I)

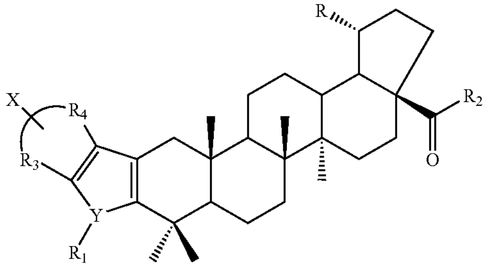

wherein X is H, Y is O, R is C(=CH$_2$)CH$_3$ or CH(CH$_3$)$_2$, $R_1$ is absent, $R_2$ is OH, $R_3$ and $R_4$ together are Ph, which comprises reacting betulonic acid of formula (IV) or 20,29-dihydrobetulonic acid of formula (V)

(IV)

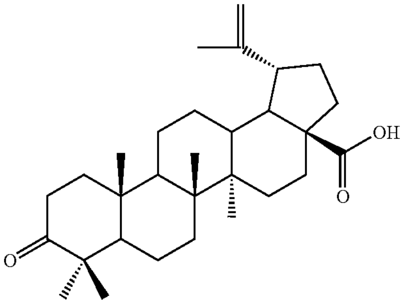

(V)

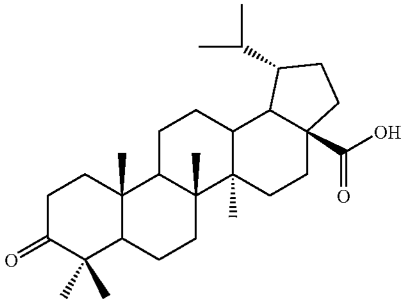

with O-phenylhydroxylamine or its hydrochloride salt.

14. A process as claimed in claim 13, wherein said reaction is carried out in the presence or absence of hydrochloric acid and in presence of a solvent selected from the group consisting of ethanol, methanol and isopropanol or a mixture of two or more thereof at a temperature ranging from 0 to 100° C.

15. A process for preparing a compound of formula (I)

(I)

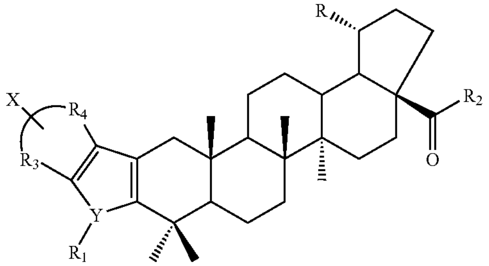

wherein, X is H or 5'—Cl; Y is N; R is C(═$CH_2$) $CH_3$ or CH(CHO 2; $R_1$ is H; $R_2$ is $OCH_2Ph$, $OCH_2C(O)OC(CH_3)_3$ or $OCH_2CH$═$CH_2$; and $R_3$ and $R_4$ together are Ph, comprises reacting a compound of the formula 14

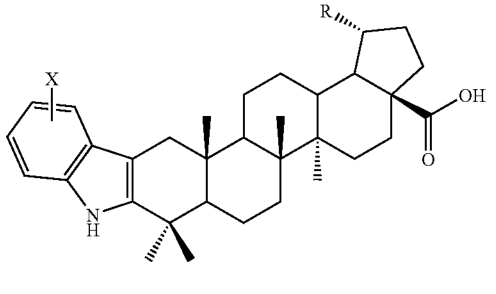

with a halide.

16. A process as claimed in claim 15, wherein said reaction is carried out in the presence of a base selected from potassium carbonate and triethylamine and with a solvent selected from acetone and ether at a temperature ranging from 0 to 100° C.

17. A process for preparing a compound of formula (I)

(I)

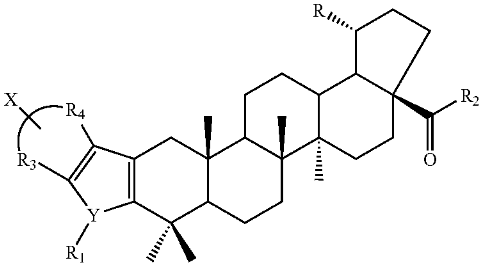

wherein X is H, or 5'Cl; Y is N; R is C(═$CH_2$) $CH_3$; $R_1$ is H; $R_2$ is

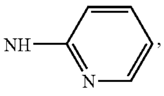,

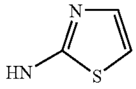, or —$NHCH_2C$≡CH; and $R_3$ and $R_4$ together are Ph; which comprises reacting a compound of formula (20)

(20)

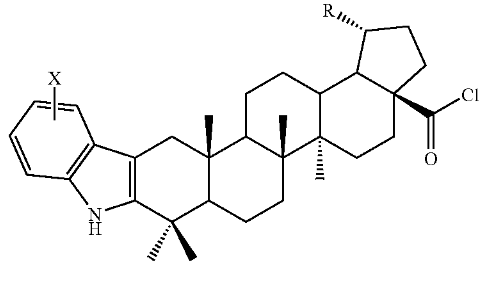

wherein, X is H or 5'Cl; Y is N; R is C(═$CH_2$)$CH_3$ or $CH(CH_3)_2$; with an amine.

18. A process as claimed in claim 17, wherein the reaction is carried out in the presence of a solvent selected from the group consisting of methylene chloride, chloroform, carbon tetrachloride, acetone and ether or a mixture of two or more thereof at a temperature ranging from 0 to 100° C.

19. A process for the preparation of a compound of formula I wherein (I)

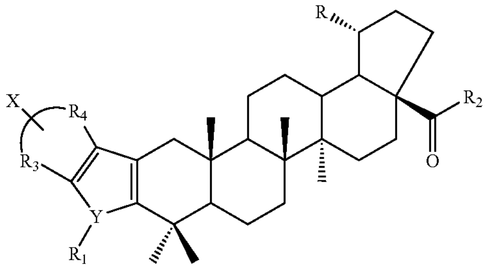

wherein X is H or 5'-Cl; Y is N'; R is C(═$CH_2$)$CH_3$, $R_1$ is H; $R_2$ is —$NHCH_2CO_2H$ and $R_3$ and $R_4$ together are Ph; which comprises reacting a compound of formula 21 or 23

(21)

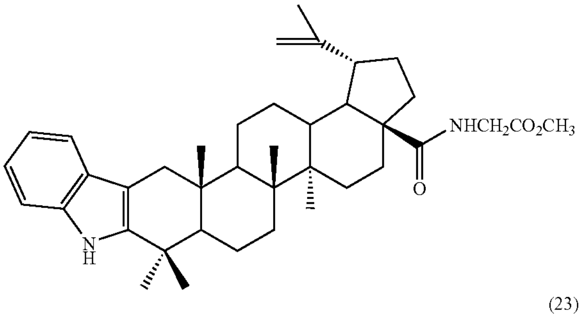

(23)

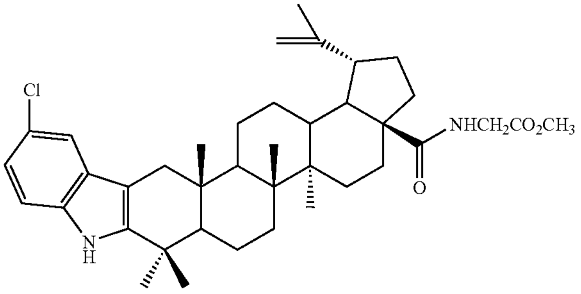

with aqueous sodium hydroxide solution.

20. The process as claimed in claim 19, wherein said reaction is carried out in the presence of a solvent selected from the group consisting of tetrahydrofuran, ethanol and methanol or a mixture of two or more thereof at a temperature ranging from 0 to 100° C.

21. A process for preparing a compound of formula (I):

(I)

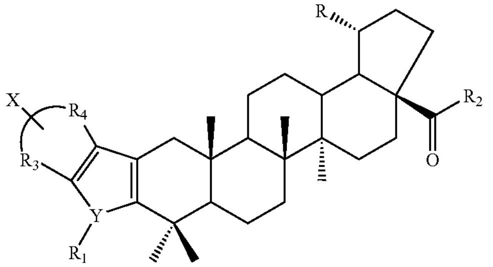

X is 5'—Cl or H, Y is N; R is $C(=CH_2)CH_3$, $R_1$ is $C_6H_5CH_2$, $R_2$ is $—NHCH_2CO_2H$; and $R_3$ and $R_4$ together are Ph; which comprises reacting a compound of formula 23 or 21

(21)

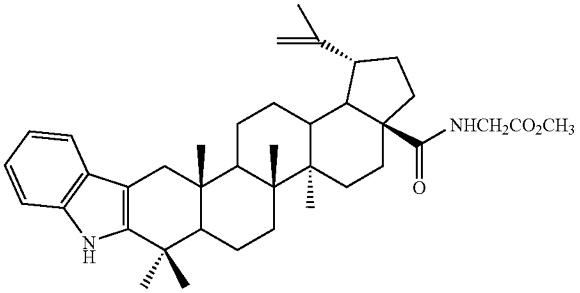

-continued (23)

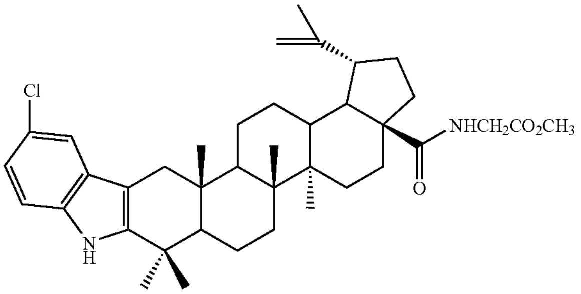

with benzyl bromide and sodium hydrazide, respectively.

22. The process as claimed in claim 21, wherein the reaction is carried out in the presence of a solvent at a temperature ranging from 0° C. to room temperature.

23. The process as claimed in claim 22, wherein the solvent is hexamethyl phosphoramide.

* * * * *